United States Patent [19]

Nestor, Jr. et al.

[11] Patent Number: 5,212,288

[45] Date of Patent: May 18, 1993

[54] TEMPORARY MINIMAL PROTECTION SYNTHESIS OF SERINE-CONTAINING POLYPEPTIDES

[75] Inventors: John J. Nestor, Jr., Cupertino; Natalie L. McClure, Portola Valley; Humberto Arzeno, Cupertino, all of Calif.

[73] Assignee: Syntex (U.S.A.) Inc., Palo Alto, Calif.

[21] Appl. No.: 654,149

[22] Filed: Feb. 8, 1991

Related U.S. Application Data

[63] Continuation-in-part of Ser. No. 482,428, Feb. 20, 1990, abandoned.

[51] Int. Cl.$^5$ ............................................. A61K 37/02
[52] U.S. Cl. ................................. 530/334; 530/328; 530/313; 530/335; 514/15
[58] Field of Search .................. 514/15; 530/313, 334, 530/335, 328

[56] References Cited

U.S. PATENT DOCUMENTS

| | | | |
|---|---|---|---|
| 3,826,794 | 7/1974 | Flouret | 260/112.5 |
| 3,842,065 | 10/1974 | Rees | 260/112.5 |
| 3,855,199 | 12/1974 | Foell et al. | 260/112.5 |
| 3,890,437 | 6/1975 | Foell et al. | 424/177 |
| 3,901,872 | 8/1975 | McKinley et al. | 260/112.5 |
| 3,928,308 | 12/1975 | Yardley | 260/112.5 |
| 3,931,140 | 1/1976 | Sarantakis | 260/112.5 |
| 3,933,782 | 1/1976 | Yardley | 260/112.5 |
| 3,941,763 | 3/1976 | Sarantakis | 260/112.5 |
| 4,108,846 | 8/1978 | Meinhofer | 260/112.5 |
| 4,234,571 | 11/1980 | Nestor et al. | 530/313 |
| 4,301,066 | 11/1981 | Bellini et al. | 260/112.5 |
| 4,317,815 | 3/1982 | Coy et al. | 424/177 |
| 4,431,635 | 2/1984 | Coy et al. | 424/177 |
| 4,481,190 | 11/1984 | Nestor et al. | 424/177 |
| 4,656,247 | 4/1987 | Folkers et al. | 530/313 |
| 4,667,014 | 5/1987 | Nestor, Jr. et al. | 530/313 |
| 4,740,500 | 4/1988 | Vale, Jr. et al. | 514/15 |
| 4,801,577 | 1/1989 | Nestor, Jr. et al. | 514/15 |
| 4,855,407 | 8/1989 | Wang | 530/334 |
| 4,859,736 | 8/1989 | Rink | 525/54.1 |
| 4,935,491 | 6/1990 | Folkers et al. | 530/313 |

OTHER PUBLICATIONS

Houghten et al. Int'l. J. Pept. Prot. Res. vol. 27 (1986) 653–58.

Coy et al. Int. J. Prot. Res. vol. 14 339–343 (1979).
Hocart et al. CA 107:134666h (1987), J. Med. Chem (1987) 30(10) 1910–14.
Hocart et al. CA 106: 120222c (1987), J. Med. Chem (1987) 30(4) 739–43.
M. Fujino, et al., Some Analogs of Luteinizing Hormone Releasing Hormone (LH–RH) Having Intense Ovulation–Inducing Activity, Biochem. Biophys. Res. Comm., 57:4, 1248–1256 (1974).
M. Bodanszky, et al., Side Reactions in Peptide Synthesis. 4. Extensive O-Acylation by Active Esters in Histidine Containing Peptides[1], J. Org. Chem., 42:1, 149–152 (1977).
D. H. Coy, et al., Minimal Side–Chain Protection Can Be A Successful Strategy in Solid–Phase Peptide Synthesis, Int. J. Peptide Protein Res., 14, 339–343 (1979).
R. A. Houghten, et al., Use of 10% Sulfuric Acid/Dioxane for Removal of N-α-Tertiary-Butyloxycarbonyl Group During Solid Phase Peptide Synthesis, Int. J. Peptide Protein Res., 27, 653–658 (1986).
J. K. Inman, Peptide Synthesis with Minimal Protection of Side–Chain Functions, The Peptides, 3, 253–302 (Academic Press, 1981).
J. Tien, et al., Novel Process for the Production of LH–RH Using CTH and Preparative HPLC, Peptide Chemistry 1987, 375–377 (Protein Research Foundation, Osaka, 1988).
K. M. Sivanandaiah, et al., Improved Solid Phase Synthesis of Luteinizing Hormone Releasing Hormone Analogues Using 9-Fluorenylmethyloxycarbonyl Amino Acid Active Esters and Catalytic Transfer Hydrogenation with Minimal Side-Chain Protection and Their Biological Activities, J. Biosci., 14:3, 311–317 (1989).

Primary Examiner—Merrell C. Cashion, Jr.
Assistant Examiner—Bennett M. Celsa
Attorney, Agent, or Firm—William Schmonsees; David A. Lowin; Tom M. Moran

[57] ABSTRACT

In a process for the solid phase synthesis of a polypeptide containing at least one serine residue, the improvement comprising temporarily protecting the side chain of the serine residue with a protecting group which is removed immediately following the addition of the serine to the peptide chain.

19 Claims, No Drawings

TEMPORARY MINIMAL PROTECTION SYNTHESIS OF SERINE-CONTAINING POLYPEPTIDES

This application is a continuation-in-part of application Ser. No. 07/482,428, filed Feb. 20, 1990, abandoned.

BACKGROUND OF THE INVENTION

1) Field of the Invention

This invention relates to the solid phase synthesis of serine-containing polypeptides, such as LH-RH agonists and antagonists, by a temporary minimal protection procedure.

2) Description of Related Art

The decapeptide LH-RH (luteinizing hormone-releasing hormone) is a neurohormone produced in the hypothalamus, which stimulates the secretion of the pituitary hormones, LH (luteinizing hormone) and FSH (follicle-stimulating hormone), which in turn act on the gonads to stimulate the synthesis of steroid hormones. The pulsatile release of LH-RH, and the consequent release of LH and FSH, controls the reproductive cycle in mammals.

LH-RH analogs are nona- or decapeptides which are structurally related to LH-RH and exhibit biological activity similar to that of LH-RH by acting on the pituitary—gonadal axis in competition with naturally occurring LH-RH. The analogs are the subject of intensive clinical investigation due to their demonstrated ability to alleviate the symptoms of endometriosis, prostate cancer, precocious puberty, and other hormonally mediated disorders. While certain LH-RH analogs are currently available for therapeutic use, their synthesis is a complicated and, consequently, expensive procedure which necessarily increases their ultimate cost. LH-RH analogs are conventionally described as either agonists or antagonists, depending upon their mode of action.

The paradoxical ability of the agonists to suppress gonadal function at high doses has been exploited in the therapeutic arena by the development and marketing of such drugs as Synarel ® nafarelin acetate nasal solution for the treatment of endometriosis. The amino acid sequence of nafarelin is as follows:

(pyro)Glu—His—Trp—Ser—Tyr—D—Nal(2)—Leu—Arg—Pro—Gly—NH$_2$.

Nafarelin and other LH-RH agonists such as leuprorelin, buserelin, goserelin, histrelin, triptorelin and deslorelin all differ from naturally occurring LH-RH by replacement of at least the glycine residue at the 6-position with a D-amino acid. The synthetic agonists then have, in common with the naturally occurring hormone, histidine at position 2, serine at position 4, tyrosine at position 5, and arginine at position 8, all of which have reactive side chains which may present synthetic difficulties.

The LH-RH antagonists directly suppress gonadotropin secretion and are, therefore, desired for their immediate and profound effects. Generally, antagonism requires deletion or replacement of the histidyl residue at position 2 in the naturally occurring hormone. From the synthetic perspective, the deletion of histidine reduces the opportunities for undesired side reactions; however, the presence of arginine, serine and tyrosine still requires that special steps be taken to avoid side reactions.

LH-RH analogs may be synthesized by various methods, such as are taught by J. M. Stewart and J. D. Young, *Solid Phase Peptide Synthesis*, W. H. Freeman Co., San Francisco, 1969; J. Meinenhofer, *Hormonal Proteins and Peptides*, Vol. 2, page 46, Academic Press (New York), 1973; and E. Schroder and K. Lubke, *The Peptides*, Vol. 1, Academic Press (New York), 1965. The methods may be broadly characterized as either solution phase or solid phase techniques. Both methods involve the sequential addition of amino acids to a growing peptide chain; however, the more rigorous conditions of solid phase synthesis generally require that any reactive side chains on the amino acids be protected during formation of the amide linkage. The side chain protecting groups may be removed concurrently with the cleavage of the completed polypeptide from the inert support on which it is made or in a separate deprotection step.

One particularly useful solid phase synthetic method for preparing LH-RH analogs is disclosed in Nestor et al., U.S. Pat. No. 4,234,571. In this commonly used approach, the α-amino (N$^\alpha$) function of each amino acid is protected by an acid sensitive group, such as t-butoxycarbonyl (Boc); any reactive side chains, as are present on arginine, serine, histidine and tyrosine, are also protected with strongly bound groups which require treatment with hydrogen fluoride or similarly drastic procedures for their removal. This use of N$^\alpha$-Boc protection and HF labile side chain protection, while adequate for the preparation of research quantities of peptides, is not entirely satisfactory for large scale production. The fully protected amino acids are expensive and require a separate step for deprotection. Further, the use of hydrogen fluoride for the final deprotection, in addition to posing serious environmental hazards, contributes to commercially unacceptable yield losses.

Alternate protocols are no more appealing. Tien et al., *Pept. Chem.* 375–379, T. Shiba and S. Sakakibara (Ed.), Protein Research Foundation, Osaka (1988), have reported the synthesis of LH-RH using tosyl protection on histidine and benzyl protection on tyrosine and serine. This approach, while avoiding the use of hydrogen fluoride, still requires a separate dehydrogenation step to remove the benzyl protecting groups, with some reduction of tryptophan occurring.

D. H. Coy et al., *Int. J. Peptide Protein Res.*, 14, 339–343 (1979) report the synthesis of the LH-RH antagonists, [D-Phe$^2$,D-Trp$^3$, D-Phe$^6$]LH-RH using a variety of side chain protection protocols, all of which require HF deprotection: providing benzyl side chain protection of serine only (with strong acid salt protection of arginine), tosyl side chain protection of arginine only, both serine and arginine side chain protection, and serine, arginine and tyrosine (with 2-bromobenzyloxycarbonyl) side chain protection. N$^\alpha$-Boc protection was employed in all cases and removed between steps with 33% trifluoroacetic acid in methylene chloride. Hydrogen fluoride was used to cleave the crude peptide from its support and to remove the side chain protecting groups. An "unprotected" synthesis employing only salt protection of arginine (as Arg.HCl) was also conducted. All of the protected syntheses gave poorer yields than that of the unprotected side chain synthesis which did not require HF treatment.

Coy et al. further reported the synthesis of the LH-RH agonist [D-Leu$^6$, desGly-NH$_2^{10}$]LH-RH ethylamide with dinitrophenyl side chain protection of histidine only, salt protection of arginine, and no HF treatment. The dinitrophenyl side chain protecting group was removed during cleavage of the peptide from its support with a solution of ethylamine in dimethylformamide. The yield from the histidine protected synthesis was 34% versus 24% for a fully protected, HF cleavage synthesis. No comparison with an unprotected synthesis was made.

The art suggests that, of the various minimal protection strategies, histidine-only protection may provide some improvement in yield over fully protected syntheses for certain LH-RH agonists; however, no particular benefit is associated with any of the reported side chain protection tactics for LH-RH antagonists.

While the ideal approach for eliminating the HF deprotection step may be to conduct an unprotected synthesis, lack of protection for histidine leads to excessive racemization. Following Coy et al., however, we have found that the use of histidine-only protection results in high levels of a bis-serine impurity. Significant improvement over the teachings of the art is needed in order to obtain a practicable minimal protection synthesis for LH-RH analogs that does not require an HF deprotection step yet provides protection for those groups which, if unprotected, will adversely affect the purity and yield of peptide.

The disclosures of the aforementioned patents and publications are incorporated by reference herein.

SUMMARY OF THE INVENTION

It is an object of this invention to provide a process for the synthesis of LH-RH analogs in which the side chains of only an essential minimal number of amino acid residues are protected.

It is a further object of this invention to provide a process for the synthesis of LH-RH analogs which obviates the need for an HF deprotection step.

It is also an object of this invention to provide a process for the synthesis of serine-containing polypeptides in which formation of serine-related impurities is inhibited.

The objects of this invention are achieved for the synthesis of serine-containing polypeptides by a process in which the side chain of the amino acid residue serine is temporarily protected with a protecting group which is removed immediately following the addition of the serine to the peptide chain. The side chain protecting group is one which is labile to the same agents useful for removing the α-amino protecting group. For those peptides which contain a histidine residue, the imidazole side chain is protected with a base sensitive group.

Temporary side chain protection of serine and side chain protection of histidine, if present, minimizes formation of impurities and maximizes yields without requiring an HF or alternative separate deprotection step.

DETAILED DESCRIPTION OF THE INVENTION

Abbreviations and Definitions

The abbreviations for the various common amino acids are those recommended by the IUPAC-IUB Commission on Biochemical Nomenclature, *Biochemistry*, 11, 1726 (1972). All peptide sequences mentioned herein are written according to the generally accepted convention whereby the N-terminal amino acid is on the left and the C-terminal amino acid is on the right.

The abbreviations herein represent L-amino acids, with the exception of the achiral amino acid glycine, and with the further exception of any unnatural amino acids which are achiral, or are otherwise designated as D- or D,L-. Et is ethyl, Bu is butyl, and iPr is iso-propyl.

Other abbreviations useful in describing the invention involve replacements of the amino acids in the natural LH-RH peptide by the following:

| Amino acid residue | Abbreviation |
|---|---|
| 3-(2-naphthyl)-alanyl | Nal(2) |
| 3-(p-fluorophenyl)-alanyl | p-F—Phe |
| 3-(p-chlorophenyl)-alanyl | p-Cl—Phe |
| 3-(3-pyridyl)-alanyl | Pal(3) |
| $N^G,N^G$-bis(ethyl)-homoarginyl | hArg(Et)$_2$ |
| $N^G,N^G$-bis(2,2,2-trifluoroethyl)-homoarginyl | hArg(CH$_2$CF$_3$)$_2$ |
| $N^G$-butyl-homoarginyl | hArg(Bu) |
| $N^\epsilon$-isopropyl-lysyl | Lys(iPr) |
| (benzyl)-histidyl | His(Bzl) |

As used herein, the term "pharmaceutically acceptable salts" refers to salts that retain the desired biological activity of the parent compound without toxic side effects. Examples of such salts are acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid, and the like.

Temporary protection means that the serine side chain is protected for a relatively short period of the synthetic cycle. The side chain protecting group and the α-amino protecting group are removed simultaneously, after the serine coupling is effected. Generally, the critical criterion for selecting the serine side chain protecting group is that the group be stable to coupling conditions but labile to α-amino deprotecting conditions. The serine side chain is preferably protected by a group selected from t-butyl, t-butyldimethylsilyl, trimethylsilyl, trityl, pivalyl, and tetrahydropyran-2-yl.

For those peptides which have histidine residues it is generally desirable to protect the imidazole side chain in order to avoid racemization during coupling. This protection may also be of the temporary variety, i.e. labile during the coupling cycle, or may remain in place until the peptide is removed from its support. Preferably, ammonolysis is used to cleave the peptide from its support and simultaneously remove the histidine protecting group. Preferred side chain protecting groups for histidine are p-toluenesulfonyl and 2,4-dinitrophenyl.

In another aspect of this invention, the deprotecting agent is selected from solutions of hydrogen chloride in C$_3$ to C$_6$ alcohols and dichloromethane. Preferably, the ratio of alcohol to dichloromethane is from 0.1 to 10.0

(v/v) and the acid concentration is 2N to 9N. Most preferably, the alcohol is i-propanol.

The temporary minimal protection process of this invention is expected to be applicable to the solid phase synthesis of any serine-containing polypeptide having a few to several dozen residues, regardless of the remainder of the sequence. LH-RH analogs, and other nona- and decapeptides, are preferred synthetic targets. While the invention is described with reference to the sequential addition of individual amino acids, those skilled in the art will recognize that the process is equally applicable to syntheses in which blocks of smaller polypeptides are coupled to form a larger polypeptide, e.g. by adding a tetrapeptide to a pentapeptide, provided that the side chains of any serine residues are temporarily protected during the serine coupling cycle.

In one embodiment of the invention there is provided an improved minimal protection process for the solid-phase synthesis of a compound having an amino acid sequence of the formula

  (I)

wherein
R$^1$ is selected from (pyro)Glu and N-Ac-D-Nal(2);
R$^2$ is selected from His, D-p-Cl-Phe and D-p-F-Phe;
R$^3$ is selected from Trp, D-Trp, D-Nal(2) and D-Pal(3);
R$^4$ is selected from D-Nal(2), D-hArg(Et)$_2$, D-Lys(iPr), D-hArg(Bu), D-hArg(CH$_2$CF$_3$)$_2$, D-His(Bzl), D-Leu, D-Pal(3), D-Ser(tBu) and D-TGrp;
R$^5$ is selected from Arg, hArg(Et$_2$), hArg(Bu), hArg(CH$_2$CF$_3$)$_2$ and Lys(iPr); and
R$^6$ is selected from Gly-NH$_2$, NH—NHCONH$_2$, D-Ala-NH$_2$ and NHEt;
wherein the amino acids are provided with N$^\alpha$ protection;
in which the improvement comprises (a) temporarily protecting the side chain of serine at position 4 and (b) protecting the side chain of histidine, if present, with a base sensitive group.

Preferably, the side chain of serine at position 4 is protected with a group labile to those agents useful for removing N$^\alpha$ protecting groups without inducing racemization, side reactions, or cleavage of the growing peptide from its resin support.

In a preferred embodiment, there is provided a process for the production of a polypeptide having the formula above wherein,
R$^1$ is (pyro)Glu or N-Ac-D-Nal(2);
R$^2$ is His or D-p-Cl-Phe;
R$^3$ is Trp or D-Pal(3);
R$^4$ is D-Nal(2), D-Leu, D-Trp, D-Ser(tBu), D-His(Bzl) or D-hArg(Et)$_2$;
R$^5$ is Arg or hArg(Et)$_2$; and
R$^6$ is Gly-NH$_2$, NHEt or D-Ala-NH$_2$.

Most preferably, the invention provides a process for the production of nafarelin, on a styrene-divinylbenzene resin, using N$^\alpha$-Boc protection, wherein,
R$^1$ is (pyro)Glu,
R$^2$ is His,
R$^3$ is Trp,
R$^4$ is D-Nal(2)
R$^5$ is Arg, and
R$^6$ is Gly-NH$_2$.

In the preferred embodiment the α-amino (N$^\alpha$) function of the amino acids is protected by an acid or base sensitive group. The protecting group is stable to the conditions of peptide bond formation, while being readily removable without destruction of the growing peptide chain or racemization of any of the chiral centers contained therein. Suitable N$^\alpha$ protecting groups are t-butoxycarbonyl (Boc), biphenylisopropyloxycarbonyl, T-amyloxycarbonyl, isobornyloxycarbonyl, α,α-dimethyl-3,5-dimethoxybenzyloxycarbonyl, o-nitrophenylsulfenyl, 2-cyano-t-butyloxycarbonyl, 9-fluorenylmethyloxycarbonyl (Fmoc) and the like. Preferably the α-amino protecting group is t-butoxycarbonyl (Boc).

The hydroxy side chain of the serine residue is protected during the coupling of serine to the growing peptide, as described for the generic embodiment of this invention. The side chain protecting group is removed after the coupling is effected and prior to adding the next amino acid. The serine side chain protecting group is removed with the same agent used to remove the N$^\alpha$ protecting group. Preferred side chain protecting groups for serine are t-butyl, t-butyldimethylsilyl, trimethylsilyl, trityl, pivalyl and tetrahydropyran-2-yl.

Further, the imidazole side chain of histidine, generally present in LH-RH agonists, is protected. The histidine side chain protecting group is base sensitive, and may be removed during the coupling cycle, but, optionally, its removal may be completed when the peptide is cleaved from its support. Preferred side chain protecting groups for histidine are p-toluenesulfonyl and 2,4-dinitrophenyl.

To initiate the synthesis the first amino acid, which will be the C-terminal amino acid in the final product, is attached to a suitable solid support. Suitable solid supports useful for the above synthesis are those materials which are inert to the reagents and reaction conditions of the stepwise condensation-deprotection reactions, as well as being insoluble in the media used. Examples of commercially available resins include styrene/divinylbenzene resins modified with a reactive group, e.g., chloromethylated styrene/divinylbenzene copolymer, hydroxymethylated styrene-divinylbenzene copolymer, and the like. Merrifield resin (1% crosslinked chloromethylated styrene/divinylbenzene copolymer) is preferred.

The attachment to the chloromethylated styrene divinylbenzene resin is made by means of the reaction of the N$^\alpha$ protected C-terminal amino acid, especially the N$^\alpha$-Boc amino acid, as its cesium, tetramethylammonium, triethylammonium, 1,5-diazabicyclo [5.4.0]undec-5-ene, or similar salt in ethanol, acetonitrile, N,N-dimethylformamide (DMF), and the like, especially the cesium salt in DMF, with the chloromethylated resin at an elevated temperature, for example between about 40° and 60° C., preferably about 50° C., for from about 12 to 72 hours, preferably about 48 hours.

The successive coupling of the protected amino acids is carried out by methods well known in the art, typically in an automated polypeptide synthesizer. Each protected amino acid is introduced in from about 1.5 to about 2.5 fold molar excess and the coupling is carried out in an inert, nonaqueous, polar solvent such as dichloromethane, DMF or mixtures thereof, preferably in dichloromethane at about ambient temperature. The coupling agent is selected from N,N'-dicyclohexylcarbodiimide (DCC), N,N'-diisopropylcarbodiimide (DIC) or other carbodiimide either along or in the presence of 1-hydroxybenzotriazole (HBt), O-acyl ureas, benzotriazole-Δ-yl-oxy-tris(pyrrolidino phosphonium) hexafluorophosphate (PyBop), N-hydroxysuccinimide, other N-hydroxyimides or oximes. Alternately, protected amino acid active esters (e.g., p-nitrophenyl, pentafluorophenyl and the like) or symmetrical anhydrides may be used.

The peptide resin is checked for complete coupling using the Kaiser Test (*Anal. Biochem.*, 34, 595 (1970)), except for the coupling to proline in which case the Chloranil Test (*Anal. Biochem.*, 117, 145 (1981)) or the Isatin Test (*Anal. Chim. Acta*, 118, 149 (1980)) is used.

If the completion test(s) suggest that the reaction is not complete, the coupling is repeated using additional amino acid but omitting additional acid deprotection. When the last coupling is completed, the resin is washed with methanol or methanol containing dichloromethane and dried at a maximum of 60° C.

At the end of each cycle, i.e., after each successive $N^\alpha$-protected amino acid is added to the growing polypeptide chain, the protecting group is removed by treatment with a deprotecting agent. After serine is incorporated, the deprotecting agent removes both the $N^\alpha$-Boc protecting group and the hydroxy side chain protecting group. The preferred deprotecting agents include hydrogen chloride in dichloromethane ($HCl/CH_2Cl_2$) and hydrogen chloride dissolved in a $C_3$-$C_6$ alcohol, preferably isopropanol, mixed with dichloromethane. Generally, the concentration of the HCl will be 2N to 9N, preferably 4N to 5N. The ratio of $CH_2Cl_2$ to the $C_3$-$C_6$ alcohol is 0.1 to 10 (v/v), preferably about 1:1. A particularly preferred deprotecting agent is 4.5N HCl in i-$PrOH$:$CH_2Cl_2$ (1:1). The deprotection step generally takes place at temperatures of 0° C. to 45° C., preferably at ambient temperatures (20° to 27° C.).

Those skilled in the art will appreciate that selection of a coupling/deprotection protocol utilizing agents other than those described above is entirely appropriate provided that the serine residue is deprotected with an agent which accomplishes the objectives of this invention. A protocol which uses $HCl/iPrOH/CH_2Cl_2$ for each deprotecting cycle may be employed. Alternatively, a mixed protocol in which $TFA/CH_2Cl_2$ is used for certain cycles and $HCl/iPrOH/CH_2Cl_2$ for others is also useful. Other cycles will be readily apparent to the skilled artisan.

When it is desired to prepare a peptide, such as buserelin or goserelin, in which $R^4$ in Formula (I) above is D-Ser(tBu), a base sensitive $N^\alpha$ protecting agent, such as Fmoc, is required for $N^\alpha$ protection. Fmoc is labile to basic agents (pH>8.5), such as piperidine, which will not remove the tBu from the D-Ser(tBu). In later cycles, following the addition of the D-Ser(tBu), it is also necessary to use base sensitive $N^\alpha$ protection. The side chain of the serine at position 4 is protected with a group which is removed with an agent which will not remove the tBu from D-Ser (t Bu), such as a mild fluoride treatment (1 equiv.) or ammonolysis. A preferred serine side chain protecting group of this embodiment is t-butyldimethylsilyl. In this manner, a D-Ser (tBu) residue may be present in the final peptide, while practicing temporary protection of the serine at position 4.

At the end of the solid phase synthesis the polypeptide is cleaved from the resin. For peptides with an alanine or glycine C-terminus, cleavage is by ammonolysis with a saturated solution of ammonia in a suitable solvent; for those peptides having a proline C-terminus, cleavage is by aminolysis with an alkylamine or fluoroalkylamine. For peptides with an alanine or glycine C-terminus, the cleavage is conducted at temperatures between about 10° and 50° C., preferably about 25° C., for between about 12 and 24 hours, preferably about 18 hours. Suitable solvents include methanol, ethanol, isopropanol, dimethylformamide, tetrahydrofuran, N,N-dimethylethanolamine, hexanes and mixtures thereof. Preferably, a saturated solution of ammonia in methanol is used. Alternatively, the peptide may be removed from the resin by transesterification with a base, followed by aminolysis.

The polypeptide is then purified by a sequence of chromatographic steps employing any or all of the following types: ion exchange on a weakly basic resin in the acetate form; hydrophobic adsorption chromatography on underivatized polystyrene-divinylbenzene (e.g., Amberlite ® XAD); silica gel adsorption chromatography; ion exchange chromatography on carboxymethylcellulose; partition chromatography (e.g., on Sephadex ® G-25), or countercurrent distribution; high performance liquid chromatography (HPLC), especially reversed-phase HPLC on octyl- or octadecylsilylsilica bonded phase column packing.

If a racemic amino acid is used in one or more of the 1, 2, 3 or 6 positions and individual isomeric products are desired, the diastereomeric nonapeptide or decapeptide final products are separated, and the desired peptide containing a D-amino acid in the appropriate position is isolated and purified, preferably during the above-described chromatographic process.

Optionally, the isolated and purified polypeptide is converted to a pharmaceutically acceptable salt.

The following Examples compare the temporary protection process of this invention with an unprotected process for both an LH-RH agonist and an LH-RH antagonists. These Examples are presented for purposes of specificity only and should not be construed so as to place any undue limitations on the scope of the claimed invention.

$N^\alpha$-Boc amino acids were obtained from Bachem (Torrance, Calif.) (Leu, Tyr, His(Tos), Arg, Trp, D-Ala and Gly), Star Biochemicals (Torrance, Calif.) (Pro and Ser(tBu)), Synthe Tech (Albany, Ore.) (D-Nal(2)), Incell (Milwaukee, Wis.) (D-Pal(3) and UCB Bioproducts (Belgium) (p-Cl-Phe).

Solutions of 4-4.5N HCl in i-$PrOH/CH_2Cl_2$(1/1) were prepared by bubbling HCl into cooled i-PrOH. Once the solution became saturated (determined by titration, approximately 9N), the solution was kept at room temperature for no more than 3 days and diluted with an equal volume of $CH_2Cl_2$ before use.

The following protocols were used to remove the $N^\alpha$-protecting group following each addition.

Program A: The resin was first washed with $CH_2Cl_2$ 1×1 min., TFA-$CH_2Cl_2$ (40/60) 1×1 min., TFA-$CH_2Cl_2$ (40/60) 1×30 min., $CH_2Cl_2$ 5×1 min., $Et_3N$-$CH_2Cl_2$ (5/95) 3×1 min., $CH_2Cl_2$ 4×1 min.

Program B: The resin was first washed with $CH_2Cl_2$ 1×1 min., 4-4.5N HCl in $CH_2Cl_2/i$-PrOH (1/1) 1×1 min., 4-4.5N HCl in $CH_2Cl_2/i$-PrOH (1/1) 1×30 min., $CH_2Cl_2$ 3×1 min., DMF 1×1 min., $Et_3N$-$CH_2Cl_2$ (5/95) 3×1 min., DMF 1×1 min., $CH_2Cl_2$ 4×1 min.

After each deprotecting and washing step, following protocol A or B, the next amino acid in sequence was added and the resin washed with $CH_2Cl_2$ 3×1 min., MeOH 4×1 min., DMF 2×1 min. and $CH_2Cl_2$ 4×1 min.

When the sequence was completed, the peptide was cleaved from the resin by treatment with a saturated solution of ammonia in methanol for about 18 hours at about 25° C.

The yields obtained in both Examples 1 and 2 using the temporary minimal protection process of this invention are significantly increased over the yields obtained in Comparative Examples 1 and 2 using unprotected syntheses.

In addition to the increase in yield, the process of this invention offers the additional advantages of employing less hazardous reagents, over a shorter time period and with lower energy expenditures in the isolation and purification of LH-RH analogs. A further advantage is the generation of smaller amounts of a considerably less toxic waste stream.

PREPARATION A

Boc-Gly-O-Resin 4.9 g of $N^\alpha$-Boc-glycine was dissolved in a mixture of 50 ml. methanol and 50 ml. distilled water. The pH of the solution was brought to 7.5 with aqueous cesium bicarbonate. The solvent was then removed under vacuum.

After 18 hours of drying under high vacuum, the residue was dissolved in 150 ml. dry DMF. 25 g 1% chloromethylated polystyrene/divinylbenzene (Merrifield) resin (corresponding to 25 mmole chloride) was added. The mixture was shaken at 50° C. for 24 hours, filtered, and the resin was then washed sequentially with DMF, water, and ethanol. The resin was dried under vacuum for 3 days to yield 28.34 g of Boc-Gly-O-Resin.

PREPARATION B

Boc-D-Ala-O-Resin

Following the procedures of Preparation A, $N^\alpha$-Boc-D-alanine was added to 1% Merrifield resin to provide $N^\alpha$-Boc-D-Ala-O-resin.

EXAMPLE 1

SYNTHESIS OF NAFARELIN WITH TEMPORARY SERINE PROTECTION

In this Example, nafarelin was prepared using the following side chain protection protocol: salt protection for arginine (as the chloride), tosyl protection for histidine His(Tos), and t-butyl protection for serine Ser(tBu).

1.0 mmol of $N^\alpha$-Boc-Gly-O-resin from Preparation A was placed in the reaction vessel of a 5.0 L Vega 296 automated solid phase peptide synthesizer fitted with accessory bottles and flasks for addition of reagents and for pressurization, depressurization and maintenance of an inert atmosphere of nitrogen.

The following amino acids were added to the $N^\alpha$-Boc-Gly-O-resin by DIC or HBt-assisted DIC coupling for 3 hours:

$N^\alpha$-Boc-Pro 2.0 equiv.
$N^\alpha$-Boc-Arg.HCl 2.0 equiv.
$N^\alpha$-Boc-Leu.H$_2$O 2.0 equiv.
$N^\alpha$-Boc-D-Nal(2) 1.5 equiv./HBt
$N^\alpha$-Boc-Tyr 1.5 equiv./HBt
$N^\alpha$-Boc-Ser(tBu) 2.0 equiv./HBt
$N^\alpha$-Boc-Trp 1.75 equiv./HBt
$N^\alpha$-Boc-His(Tos 1.75 equiv./HBt
(pyro)Glu 2.5 equiv./HBt Program A was used to remove the $N^\alpha$ protecting groups on Gly, Pro, Arg, Leu, D-Nal(2) and Tyr. Program B was used for the removal of the $N^\alpha$ protecting groups on Ser, Trp, and His and for the removal of the serine side chain protecting group.

The crude peptide was dissolved in 2M acetic acid and converted to the acetate salt by passage through a column of AG3-X4A resin (Bio-Rad). The acetate was dissolved in a minimal amount of methanol and acetone added to reprecipitate the peptide. Reversed phase HPLC (Partisil ODS-3, 40μ, acetonitrile with 0.5% acetic acid) was used to remove polar and non-polar impurities. Fractions containing at least 97% nafarelin acetate were combined, diluted with water, reloaded on a reversed-phase HPLC column, and washed with 1% acetic acid in water. The residue was precipitated, filtered, washed with ether and dried under vacuum.

Amino acid analyses were performed on a Beckman 119CL amino acid analyzer. Samples for amino acid analyses were hydrolyzed with 4N CH$_3$SO$_3$H (0.2% 3-(2-aminomethyl indole) HCl) for 20 hrs at 110° C.

Analytical HPLC was performed on a Spectra Physics 8800 chromatograph, using an ODS-II column from Alltech, 5μ, 4.6×250 mm, 10 μl inj., flow - 1.5 ml/min., 27.5% CH$_3$CN, 72.5% 0.16M KH$_2$PO$_4$ pH=5.1, temp.=40° C.

HPLC analysis of the crude peptide showed a main peak with a retention time (rt) of 18 min. corresponding to nafarelin and no impurity over 1% at rt 14 min.

COMPARATIVE EXAMPLE 1

SYNTHESIS OF NAFARELIN WITHOUT SERINE PROTECTION

The procedure of Example 1 was followed except that $N^\alpha$-Boc-Ser was substituted for $N^\alpha$-Boc-Ser(tBu).

HPLC analysis showed a main peak at 18 min. corresponding to nafarelin and 8.1 to 11.5% of an impurity at a retention time (rt) of 14 min.

The yield from this "unprotected" synthesis was approximately the same as that obtained from a fully protected synthesis and significantly lower than that achieved with the temporary protection synthesis of Example 1.

EXAMPLE 2

SYNTHESIS OF GANIRELIX USING TEMPORARY SERINE PROTECTION

In this Example an LH-RH antagonist, ganirelix, N-Ac-Nal(2)-D-pCl-Phe-D-Pal(3)-Ser-Tyr-D-hArg-(Et)$_2$-Leu-hArg(Et)$_2$-Pro-Ala-NH$_2$, was prepared using the following side chain protection protocol: salt protection for L- and D-hArg(Et)$_2$ (as the chloride) and t-butyl protection for serine.

Amino acids were added to the $N^\alpha$-Boc-D-Ala-O-Resin of Preparation B in the following sequence:

$N^\alpha$-Boc-Pro 2.3 equiv.
$N^\alpha$-Boc-hArg(Et)$_2$.HCl 1 equiv./HBt
$N^\alpha$-Boc-Leu.H$_2$O 2.3 equiv.
$N^\alpha$-Boc-D-hArg(Et)$_2$.HCl 1.6 equiv./HBt
$N^\alpha$-Boc-Tyr 2.1 equiv./HBt
$N^\alpha$-Boc-Ser(tBu) 2.0 equiv.
$N^\alpha$-Boc-D-Pal(3) 1.8 equiv./HBt
$N^\alpha$-Boc-D-p-Cl-Phe 2.0 equiv.
$N^\alpha$-Boc-D-Nal(2) 2.1 equiv./HBt
Acetic anhydride An acetylation (capping of the resin) was done after Ala, Pro and Leu. Excess HBt (2 equiv.) was used for the coupling of the basic amino acids, hArg(Et)$_2$ and Pal(3).

Program A was used for the removal of the protecting groups on Ala, Pro, L-hArg(Et)2, Leu and D-Nal(2); Program B was used for the removal of the protecting groups on D-hArg(Et)2, Tyr, Ser, D-Pal(3) and p-Cl-Phe.

The crude peptide was first dissolved in 2M acetic acid and converted to its acetate salt by passage through a column of AG3-X4A resin (Bio-Rad). The acetate was subjected to chromatography on a silica gel column (Cl2/i-PrOH/MeOH/H2O/HOAc solvent); the acetate fractions dissolved in H2O and loaded onto a reversed-phase column (Vydec C-18, 15-20µ), and purified using acetonitrile/TEAP (pH 3). Fractions of the desired purity were combined and diluted with water and reloaded on a reversed-phase HPLC column, then washed with 1% acetic acid in water. The peptide was stripped with a mixture of MeOH/CH3CN/HOAc/H2O (44/50/1/5). The residue was dissolved in acetic acid and precipitated over ether, filtered, washed with ether and dried under vacuum.

Amino acid analyses were performed on a Beckman 119CL amino acid analyzer. Samples for amino acid analyses were hydrolyzed with 6N HCl at 110° C. for 20 hrs.

Analytical HPLC was performed on a Spectra Physics 8800 chromatograph, using a Spherisorb C-8 (Alltech), 5µ, 4.6×250 mm, 10 µl inj., flow=1.5 ml/min., 30% CH3CN, 70% NH4H2PO4 0.04M, dimethyloctylamine $4.3 \times 10^{-3}$, temp. 40° C.

Snythesis of ganirelix was confirmed by the presence of a main peak at rt 18 min.; no other peak over 1% was noted at rt 16 min.

COMPARATIVE EXAMPLE 2

SYNTHESIS OF GANIRELIX WITHOUT TEMPORARY SERINE PROTECTION

Example 2 was repeated using $N^\alpha$-Box-Ser instead of $N^\alpha$-Boc-Ser(tBu).

HPLC analysis showed the presence of a main peak at 18 min. corresponding to ganirelix and the presence of an impurity in 6.5% at rt 16 min.

The following claims particularly point out and distinctly claim the subject matter which applicants regard as their invention. These claims are entitled to the full range of equivalents recognizable by those skilled in the art of solid phase peptide synthesis.

What is claimed is:

1. In a process for the solid phase synthesis of a LH-RH analog having at least one serine, the improvement comprising temporarily protecting the side-chain of each serine residue with a protecting group labile to $N^\alpha$-deprotecting agents wherein the serine side-chain protecting group and the $N^\alpha$-protecting group are removed immediately following the addition of each serine to the polypeptide chain, prior to adding the next amino acid in the sequence.

2. A process of claim 1 in which the serine side chain protecting group is selected from the group consisting of t-butyl, trityl, t-butyldimethylsilyl, trimethylsilyl, and tetrahydropyran-2-yl.

3. A process of claim 2 in which the serine side chain protecting group is removed by treatment with a reagent selected from the group consisting of HCl/CH2Cl2, TFA/CH2Cl2, and HCl/(C3-C6) alcohol/CH2Cl2.

4. A process of claim 3 in which the C3-C6 alcohol is isopropanol.

5. In a process for the solid-phase synthesis of a compound having an amino acid sequence of the formula $$R^1\text{-}R^2\text{-}R^3\text{-Ser-Tyr-}R^4\text{-Leu-}R^5\text{-Pro-}R^6 \qquad (I)$$

wherein
 $R^1$ is selected from (pyro)Glu and N-Ac-D-Nal(2);
 $R^2$ is selected from His, D-p-Cl-Phe and D-p-F-Phe;
 $R^3$ is selected from Trp, D-Trp, D-Nal(2) and D-Pal(3);
 $R^4$ is selected from D-Nal(2), D-hArg(Et)2, D-Lys(iPr), D-hArg(Bu), D-hArg(CH2,CF3)2, D-His(Bzl), D-Leu, D-Pal(3), D-Ser(tBu) and D-Trp;
 $R^5$ is selected from Arg, hArg(Et)2, hArg(Bu), hArg(CH2, CF3)2 and Lys(iPr); and
 $R^6$ is selected from Gly-NH2, NH-NHCONH2, D-Ala-NH2 and NHEt;
 wherein the amino acids are provided with $N^\alpha$ protection;
 the improvement comprising temporarily protecting the side chain of serine at position 4 with a side chain protecting group labile to $N^\alpha$-deprotecting agents, wherein the serine side chain protecting group and the $N^\alpha$-protecting group are removed immediately following the addition of the serine to the polypeptide chain, prior to addition of the next amino acid in the sequence.

6. A process of claim 5 in which the serine side chain protecting group is selected from the group consisting of t-butyl, trityl, tetrahydropyranyl, trimethylsilyl, and t-butyl-dimethylsilyl.

7. A process of claim 6 in which the serine side chain protecting group is t-butyl.

8. A process of claim 5 in which the $N^\alpha$ protecting group is selected from t-butoxycarbonyl, t-amyloxycarbonyl, isobornyloxycarbonyl, α,α-dimethyl-3,5-dimethoxybenzyloxycarbonyl, o-nitrophenylsulfenyl, 2-cyano-t-butoxycarbonyl, and 9-fluorenylmethyloxycarbonyl.

9. A process of claim 5 in which the $N^\alpha$ protecting group is t-butoxycarbonyl, the serine side chain protecting group is t-butyl, and the histidine side chain protecting group is p-toluenesulfonyl.

10. A process of claim 5 in which
 $R^1$ is N-Ac-D-Nal(2);
 $R^2$ is D-p-Cl-Phe;
 $R^3$ is D-Pal(3);
 $R^4$ is D-hArg(Et)2;
 $R^5$ is L-hArg(Et)2; and
 $R^6$ is D-Ala-NH2.

11. A process of claim 6 in which
 $R^1$ is (pyro)Glu;
 $R^2$ is His;
 $R^3$ is Trp;
 $R^4$ is D-Nal(2), D-Leu, D-Ser(tBu), D-His(Bzl) or D-Trp;
 $R^5$ is Arg; and
 $R^6$ is Gly-NH2, NHNHCONH2 or NHEt.

12. A process of claim 11 in which
 $R^4$ is D-Nal(2) and $R^6$ is Gly-NH2.

13. A process of claim 5 in which the deprotecting agent is selected from HCl/CH2Cl2, TFA/CH2Cl2, and HCl/(C3-C6) alcohol/CH2Cl2.

14. A process of claim 5 in which the deprotecting agent is HCl/iPrOH/CH2Cl2.

15. A process of claim 5 in which the $N^\alpha$-protecting group is t-butoxycarbonyl, the serine side chain protecting group is t-butyl, and the deprotecting agent is HCl/iPrOH/CH$_2$Cl$_2$.

16. A process for the solid phase synthesis of nafarelin comprising successively coupling of an inert solid support the following N$^\alpha$protected amino acids:

N$^\alpha$-Boc-Gly
N$^\alpha$-Boc-Pro
N$^\alpha$-Boc-Arg.HCl
N$^\alpha$-Boc-Leu
N$^\alpha$-Boc-D-Nal(2)
N$^\alpha$-Boc-Tyr
N$^\alpha$-Boc-Ser(protected)
N$^\alpha$-Boc-Trp
N$^\alpha$-Boc-His(protected)
N$^\alpha$-Boc-(pyro)Glu, treating the product between each step-wise addition with a solution of HCl/iPrOH/CH$_2$Cl$_2$ at temperatures of 0° C. to 45° C. and then cleaving the nafarelin from the support by treatment with a saturated solution of ammonia at a temperature of 10° to 50° C.

17. A process of claim 16 in which Ser(protected) is Ser(tBu) and His(protected is His(Tos).

18. A process for the solid phase synthesis of ganirelix comprising successively coupling on an inert solid support the following N$^\alpha$protected amino acids, N$^\alpha$-Boc-D-Ala;
N$^\alpha$-Boc-Pro;
N$^\alpha$-Boc-hArg(Et)$_2$.HCl;
N$^\alpha$-Boc-Leu;
N$^\alpha$-Boc-D-hArg(Et)$_2$.HCl;
N$^\alpha$-Boc-Tyr;
N$^\alpha$-Boc-Ser(protected);
N$^\alpha$-Boc-D-Pal(3);
N$^\alpha$-Boc-D-p-Cl-Phe;
N$^\alpha$-Boc-Ac-D-Nal(2);

treating the product between each step-wise addition with a solution of HCl/iPrOH/CH$_2$Cl$_2$ at temperatures of 0° C. to 45° C. and then cleaving the ganirelix from the support by treatment with a saturated solution of ammonia at a temperature of 10° to 50° C.

19. A process of claim 18 in which Ser(protected) is Ser(tBu).

* * * * *